United States Patent
Aguila et al.

(10) Patent No.: US 10,676,764 B2
(45) Date of Patent: *Jun. 9, 2020

(54) PRODUCTION OF D-SORBITOL BY HYDROGENATION

(71) Applicant: DSM IP ASSETS B.V., Heerlen (NL)

(72) Inventors: Mae Joanne Aguila, Kaiseraugst (CH); Hans-Peter Hohmann, Kaiseraugst (CH); Laurent Lefort, Kaiseraugst (CH); Jonathan Alan Medlock, Kaiseraugst (CH); Guenter Pappenberger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/742,094

(22) PCT Filed: Jul. 14, 2016

(86) PCT No.: PCT/EP2016/066711
§ 371 (c)(1),
(2) Date: Jan. 5, 2018

(87) PCT Pub. No.: WO2017/009403
PCT Pub. Date: Jan. 19, 2017

(65) Prior Publication Data
US 2018/0201959 A1    Jul. 19, 2018

(30) Foreign Application Priority Data
Jul. 14, 2015 (EP) .................................. 15176658

(51) Int. Cl.
*C12P 7/18* (2006.01)
*C12N 9/04* (2006.01)
*C07C 29/149* (2006.01)

(52) U.S. Cl.
CPC .............. *C12P 7/18* (2013.01); *C07C 29/149* (2013.01); *C12N 9/0006* (2013.01); *C12Y 101/99028* (2013.01)

(58) Field of Classification Search
CPC ......... C07C 29/149; C07C 31/26; C12P 7/18; C12N 9/0006; C12Y 101/99028
USPC ................................ 435/105, 100, 137, 189
See application file for complete search history.

(56) References Cited

U.S. PATENT DOCUMENTS 7,968,704 B2    6/2011  Hirth et al.
2006/0009661 A1    1/2006  Arndt et al.

OTHER PUBLICATIONS

Devos et al., (Proteins: Structure, Function and Genetics, 2000, vol. 41: 98-107.*
Kulmanov et al. Bioimormatics 2018, 34(4) pp. 660-668.*
Witkowski et al., (Biochemistry 38:11643-11650, 1999.*
Kisselev L., (Structure, 2002, vol. 10: 8-9.*
Silveria et al.( Appl Micr Biotech 2001, 55, pp. 442-445.*
Goldberg et al ( JBC 1989, 264, pp. 9901-9904.*
Hashiguchi et al ( JACS 1995, 117 pp. 7562-7563.*
Noyori et al ( Acc Chem Res 1997, 30 pp. 97-102.*
International Search Report for PCT/EP2016/066711, dated Oct. 11, 2016, 3 pages.
Written Opinion of the ISA for PCT/EP2016/066711, dated Oct. 11, 2016, 6 pages.
D. Ranken et al (1997). Food Industries Manual (24th ed.). London, UK: Blackie Academic & Professional. pp. 407-408.

* cited by examiner

*Primary Examiner* — Robert B Mondesi
*Assistant Examiner* — Mohammad Y Meah
(74) *Attorney, Agent, or Firm* — Nixon & Vanderhye P.C.

(57) ABSTRACT

The present invention relates to a novel and inventive process for the production of sorbitol from D-sucrose.

8 Claims, No Drawings

PRODUCTION OF D-SORBITOL BY HYDROGENATION

This application is the U.S. national phase of International Application No. PCT/EP2016/066711 filed 14 Jul. 2016, which designated the U.S. and claims priority to EP Patent Application No. 15176658.1 filed 14 Jul. 2015, the entire contents of each of which are hereby incorporated by reference.

The present invention relates to a novel and inventive process for the production of D-sorbitol from sucrose.

Nowadays, most D-sorbitol is made from corn syrup, but it is also found in apples, pears, peaches, and prunes. In below text, it is referred to as sorbitol.

Sorbitol can be also obtained from sucrose, wherein hydrolyzed sucrose or any combination of D-fructose and D-glucose is converted in a biotransformation process using the enzyme glucose-fructose oxidoreductase (GFOR), for example from *Zymomonas mobilis*, to form an equimolar mixture of D-glucono-1,5-lactone (in below text referred to as gluconolactone) and sorbitol [Jonas, R. and Silveira, M. M. (2004), Appl. Biochem. Biotech. 118, 321-336], from which sorbitol has to be isolated via one or several purification steps. As a consequence, production costs are rather high production with rather low yield and purity of sorbitol obtained from such process.

Thus, there is a need for a more efficient and cost effective industrial process for the production of sorbitol.

Surprisingly, we found a process for sorbitol production free of gluconolactone by-product, wherein sucrose can be used as starting material, wherein the process comprises the step of transition metal-based catalyzed hydrogenation to form sorbitol in very high yields.

Thus, the present invention relates to a process (process P) for the production of sorbitol from sucrose comprising a hydrogenation step in the presence of a transition metal-based complex. For the purpose of the present invention, the sucrose might in a first step be enzymatically or chemically converted leading to a mixture of several components as starting material/substrate for the hydrogenation step described herein.

For the purpose of the present invention, the term "transition metal-based complex" includes catalytic complexes comprising a transition metal catalyst, in particular wherein the transition metal is selected from the group consisting of Ru, Ir, Pd, Pt, Rh, Fe, Co, Os and Ni (process P1). Preferably, the transition metal is selected from Ru or Ir (process P2).

The complex may furthermore include one or more organic ligand(s), in particular organic ligand(s) with nitrogen, phosphorus and/or carbene-type donor(s). If the transition metal is Ru, the organic ligand preferably contains at least one nitrogen as donor. More preferred are organic ligands containing (1) at least one nitrogen donor and at least one phosphorus donor or (2) at least one nitrogen donor and at least one carbene-type donor. If the transition metal is Ir, the organic ligand preferably contains at least one nitrogen donor.

Thus, the present invention relates to a process (P3), which is process (P), (P1), or (P2), wherein the complex includes one or more organic ligands.

Furthermore, the present invention relates to process (P4), which is process (P3) and using ligand(s) with nitrogen, phosphorus and/or carbene-type donor(s).

Particularly, the transition metal-based complexes are selected from the ones shown in formula (III) to (VIII) below:

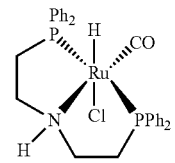
(III)

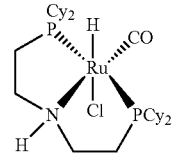
(IV)

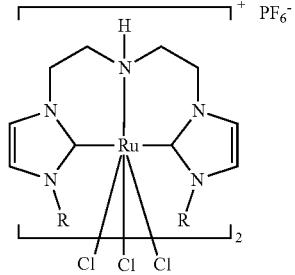
(V)

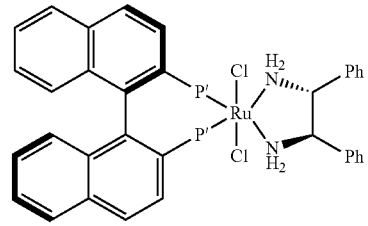
(VI)

0.5 equiv [Ir(COE)$_2$Cl]$_2$

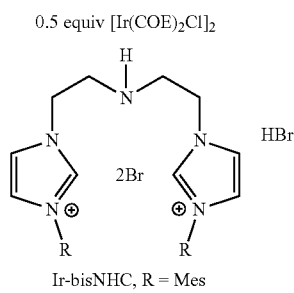

Ir-bisNHC, R = Mes 0.5 equiv [Ir(COE)$_2$Cl]$_2$

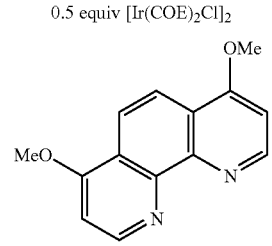
(VIII)

Thus, the present invention is directed to a process (P5), which is process (P4) with the transition metal-based complex selected from a complex according to formula (III) to (VIII).

The transition metal-based complexes as described herein, and in particular the ones according to formula (III) to (VIII) are known as such—but used for other purposes—and thus obtainable from commercial sources (STREM chemicals Inc.; Sigma-Aldrich Chemicals).

Processes for production of all transition metal-based complexes used for the purpose of the present invention including the ones of formula (III) to (VIII) are known in the art. Said complexes may be formed from a metal precursor and, optionally, an organic ligand or may be formed in situ.

Thus, the present invention is directed to the production of sorbitol from sucrose comprising a hydrogenation step, said hydrogenation comprising the conversion of the respective substrate in the presence of a transition metal-based complex mentioned above to form sorbitol in very high yields, including but not limited to yields in the range of at least 87%, such as e.g. at least 90 or 95%, preferably in the range of at least 98%. In particular, said conversion is performed in the presence of a transition metal-based complex comprising a transition metal selected from the group consisting of Ru, Ir, Pd, Pt, Rh, Fe, Os, Co and Ni, preferably Ru or Ir, which is preferably combined with one or more organic ligand(s), in particular organic ligand(s) containing one or more nitrogen, phosphorus and/or carbene-type donor(s). More particularly, said conversion is performed in the presence of a transition metal-based complex comprising Ru or Ir as transition metal and one or more organic ligands, wherein if the transition metal is Ru, the organic ligand preferably contains at least one nitrogen as donor, more preferably at least one nitrogen donor and at least one phosphorus donor or at least one nitrogen donor and at least one carbene-type donor. If the transition metal is Ir, the organic ligand preferably contains at least one nitrogen donor. Even more particularly, said conversion is performed in the presence of a transition metal-based complex comprising one of the transition metal-based complexes shown in formula (III) to (VIII) above.

Suitable substrate/starting material for the hydrogenation step in production of sorbitol is the product of an enzymatic bioconversion step wherein hydrolyzed sucrose is converted in the presence of the enzyme glucose-fructose oxidoreductase (GFOR). Methods for hydrolysis of sucrose are known [M. D. Ranken, Christopher G J Baker, R. C. Kill, ed. (1997). Food Industries Manual (24th ed.). London, UK: Blackie Academic & Professional. pp. 407-408]. The product of said bioconversion can directly be used for the process as described herein, with the proviso that residual water from the bioconversion process is removed. Methods to generate such water-free substrates are known.

Thus, the present invention relates to process (P6), which is process (P), (P1), (P2), (P3), (P4), or (P5), wherein the product of the bioconversion of hydrolyzed sucrose in the presence of GFOR is used as starting material or substrate for the hydrogenation step described herein.

In one aspect, the hydrogenation step as described herein in the presence of a transition metal-based complex is catalyzed homogeneously.

Usually, such processes according to the present invention are carried out in a solvent or a mixture of solvents. Suitable solvents are non-aqueous, organic or polar solvents, such as e.g. alcohols (including, but not limited to, methanol, ethanol, propanol, etc.), ethers (including, but not limited to, THF) or amides. Preferably, alcohols are used as solvents in the hydrogenation step as described herein.

Thus, in one embodiment the present invention is related to a process (P7), which is process (P), (P1), (P2), (P3), (P4), (P5) or (P6), wherein the transition metal-based hydrogenation step is carried out in the presence of a solvent.

Preferred is the process (P8), which is process (P7), wherein the solvent is selected from non-aqueous, organic or polar solvent. More preferred is the process (P9), which is process (P8), wherein the solvent is alcohol.

Usually, such processes according to the present invention are furthermore carried out under pressure, such as e.g. in the presence of $H_2$ gas during the hydrogenation step. In a particular embodiment, a process as described herein according to the invention is carried out under pressure, in particular with a pressure of at least about 2, 5 or 10 bar and/or not more than about 200, 100 or 60 bar, such as in particular with a pressure of from about 2 bar to about 200 bar, preferably from about 5 bar to about 100 bar, more preferably from about 10 bar to about 60 bar. Preferably, said pressure is achieved in the presence of $H_2$ gas.

Thus, the present invention relates to a process (P10), which is process (P), (P1), (P2), (P3), (P4), (P5), (P6), (P7), (P8) or (P9), wherein the process is carried out under pressure. Preferably, the present invention relates to process (P11), which is process (P10) in the presence of $H_2$ gas. One embodiment of the present invention is directed to process (P12), which is process (P10) or (P11), wherein the pressure is in the range from about 2 bar to about 200 bar, preferably to process (P13), which is process (P12), wherein the pressure is in the range from about 5 bar to about 100 bar, more preferably to process (P14), which is process (P13), wherein the pressure is in the range from about 10 to about 60 bar.

Usually, such processes according to the present invention are furthermore carried out at elevated temperature including room temperature, such as e.g. in the presence of elevated temperature during the hydrogenation step. The term "elevated temperature" includes but is not limited to temperature which is above room temperature, e.g. at least 25° C. and above (typically a temperature of at least 30° C. to 40° C.). In a particular embodiment, a process as described herein according to the invention is carried out at a temperature of at least about 20° C. or 30° C. and/or of not more than about 150° C. or 100° C., in particular at a temperature in the range of about 20° C. to about 150° C., preferably in a range of about 30° C. to about 100° C.

Thus, the present invention relates to a process (P15), which is process (P), (P1), (P2), (P3), (P4), (P5), (P6), (P7), (P8), (P9), (P10), (P11), (P12), (P13) or (P15), wherein the hydrogenation step is carried out at elevated temperature. In particular, it relates to process (P16), which is process (P15), wherein the temperature is in the range of about 20° C. to about 150° C., more particularly to a process (P17), which is process (P16), wherein the temperature is in the range of about 30° C. to about 100° C.

Usually, such processes according to the present invention are furthermore carried out at a defined molar ratio of substrate to catalyst (referred herein as S/C ratio), such as e.g. a defined S/C ratio during the hydrogenation step. In a particular embodiment, a process as described herein according to the invention is carried out at a defined S/C ratio in the range of about 50 to about 100000, preferably of about 100 to about 40000, more preferably of about 5000 to about 30000.

Thus, the present invention relates to a process (P18), which is process (P), (P1), (P2), (P3), (P4), (P5), (P6), (P7), (P8), (P9), (P10), (P11), (P12), (P13), (P14), (P15), (P16) or (P17) wherein the S/C ratio is in the range of about 50:about 100000. In particular, it relates to process (P19), which is process (P18), wherein the S/C ratio is in the range of about 100:about 40000, more particularly to a process (P20), which is process (P19), wherein the S/C ratio is in the range of about 5000:about 30000.

The process according the present invention can also be carried out in the presence of at least one base, preferably at least one alkoxide base (i.e. NaOCH$_3$, KOCH$_3$, NaOi-propanol, KOi-propanol, NaOtbutanol, KOtbutanol).

Thus, the present invention relates to a process (P21), which is a process (P), (P1), (P2), (P3), (P4), (P5), (P6), (P7), (P8), (P9), (P10), (P11), (P12), (P13), (P14), (P15), (P16), (P17), (P18), (P19) or (P20), wherein the process is carried out in the presence of at least one base. Preferably, to a process (P22), which is process (P21), wherein the base is at least one alkoxide base, more preferably process (P23), wherein the base is selected form the group consisting of NaOCH$_3$, KOCH$_3$, NaOi-propanol, KOi-propanol, NaOtbutanol and KOtbutanol.

The sorbitol formed by a process according to any one of process (P), (P1), (P2), (P3), (P4), (P5), (P6), (P7), (P8), (P9), (P10), (P11), (P12), (P13), (P14), (P15), (P16), (P17), (P18), (P19), (P20), (P21), (P22) or (P23) is obtained in excellent yields. The yields, which are obtained are significantly higher than those from the prior art processes.

The product can be purified (when needed) using commonly known methods. However, and furthermore advantageously over the prior art, the process of the present invention leads to complete conversion of sucrose to sorbitol without formation of significant amounts, e.g. less than 10%, 5% or even less than 2%, of by-products such as e.g., gluconolactone.

The invention is illustrated by the following Examples. All percentages are related to the weight.

EXAMPLE 1: HYDROGENATION OF GLUCONOLACTONE-SORBITOL MIXTURES

General Procedure for Hydrogenation: Samples of gluconolactone and sorbitol samples in various ratios (1.0 mmol total substrate amount) were weighed into 5-mL crimp vials and transferred in N$_2$-filled glovebox. All further manipulations were done in the N$_2$-filled glovebox. Into these samples, KOMe solution in methanol (5 mol % wt total substrate) and catalyst solution/slurry in methanol (0.5 mol % wt total substrate, S/C 200) were added; volume was further diluted to 3.0 mL with methanol. These vials were capped with PTFE coated septum and placed inside a Premex 96er parallel hydrogenation reactor. The system was purged with N$_2$ (3×10 bar) and H$_2$ (3×10 bar). The reactions were carried out at 50 bar H$_2$, 70° C. for 16 h with stirring (300 rpm). After the reaction, HPLC samples were prepared in deionized H$_2$O. Concentrations of the gluconolactone and sorbitol in the reaction were determined using calibration curves.

Analysis: Products were analyzed with HPLC using Agilent Technologies 1260 Infinity instrument equipped with Waters 2414 Refractive Index Detector. The parameters are column: BIORAD Aminez-HPX-87H, 300×7.8 mm, column temperature: 50° C., flow rate: 0.55 mL/min, injection volume: 100 µL, eluent: 5 mM H$_2$SO$_4$(aq), collection time: 60 min. Retention times, min: gluconolactone=9.6, sorbitol=10.9.

TABLE 1

Gluconolactone (Glul)-to-sorbitol (Sor) ratio using the transition metal-based complex of formula (III) as catalyst (Conditions: 1 mmol total amount of gluconolactone and sorbitol at varying ratios, 5 mol % KOMe, 0.5 mol % of complex according to formula (III), 3 mL total volume methanol, 50 bar H$_2$, 70° C., 16 h, HPLC analysis in H$_2$O, DF = 168).

| Glucl:Sor ratio | Glucl [mM] | Sor [mM] | Conversion [%] |
|---|---|---|---|
| 1:9 | 5.3 | 391 | 87 |
| 3:7 | 5.6 | 388 | 95 |
| 7:3 | 9.2 | 477 | 97 |
| 9:1 | 10.2 | 401 | 97 |
| 10:0 | 8.9 | 379 | 98 |

EXAMPLE 2: PRODUCTION OF SORBITOL FROM SUCROSE UNDER STANDARD CONDITIONS

A modified strain of *Zymomonas mobilis* ATCC 29191 devoid of gluconolactonases activity is obtained by knock-out of the known genes for this activity [Kanagasundaram V, Scopes R. 1992 Biochim Biophys Acta, 1171(2), 198-200].

Biomass of gluconolactonase-deficient *Zymomonas mobilis* ATCC 29191 is produced by cultivation on 100 g/l glucose, 5 g/l yeast extract, 0.5 g/l of potassium dihydrogen phosphate, 0.5 g/l of magnesium sulfate (7H$_2$O), 20 mg/l of ammonium ferrous sulfate (6H$_2$O), 1 mg/l of biotin, and 2 mg/l of calcium pantothenate at pH 7.0 and 28° C. After cultivation, the culture broth is centrifuged to harvest the biomass and washed with isotonic saline (8.5 g/l).

The biomass is treated with toluene (10% v/v in pH 7 buffer) in order to increase the permeability.

A 3 ml aqueous solution is prepared, containing 0.5 g (wet weight) toluene-treated biomass together with 0.81 g glucose and 0.81 g fructose, corresponding to a concentration of 1.5 M for each sugar. The reaction temperature is maintained at 39° C. and the pH at 6.2 by the addition of 2M Na$_2$CO$_3$. Over 420 min, 96% of the substrate are converted, with essentially equivalent amounts of both gluconolactone and sorbitol produced.

The biomass is separated from the reaction mixture by centrifugation. Then, 0.33 ml of the supernatant is lyophilized to remove water and the dried material is dissolved in 3 ml methanol and used as starting material/substrate (=gluconolactone and sorbitol equimolar mix) for the following hydrogenation step.

Exemplified is a hydrogenation using a transition metal-based complex according to formula (III) as catalyst (Conditions: 1 mmol total amount of starting material, 5 mol % KOMe, 0.5 mol % of complex according to formula (III), 3 mL total volume methanol, 50 bar H$_2$, 70° C., for 16 h, HPLC analysis in H$_2$O, DF=168), resulting in a conversion yield of gluconolactone to sorbitol of more than 95% or a conversion yield of sucrose to sorbitol in the range of 92%.

EXAMPLE 3: HYDROGENATION USING DIFFERENT TRANSITION METAL-BASED COMPLEXES

To test the influence of different transition-metal based complexes used in the hydrogenation step, the starting material/substrate for the different reactions obtained according to Example 2, with removal of water and dissolving methanol (see above), is used with all transition metal-based complexes according to formula (IV) to (VIII) as described herein for the catalytic reaction. The best results are obtained with a complex according to formula (III) and (V), with a yield of sorbitol from sucrose in the range of at least 91%.

EXAMPLE 4: HYDROGENATION USING DIFFERENT SOLVENTS

To test the influence of the solvent used in the hydrogenation step, production of the starting material is obtained as described (Example 2) with the proviso that the dried material is dissolved in different solvents. The reaction (standard conditions, i.e. use of transition metal-based complex (III), with conditions described in Example 2) works best with alcoholic solvents, including methanol, ethanol or isopropanol, with conversion rates in the range of from 82% (isobutanol) to 96% (ethanol) to 98% (methanol) with regards to conversion of the starting material to sorbitol.

EXAMPLE 5: HYDROGENATION USING DIFFERENT SUBSTRATE TO CATALYST RATIOS

To test the influence of the S/C ratio used in the hydrogenation step, production of the starting material is obtained as described (Example 2) with the proviso that different amounts of substrate is used for the reaction (standard conditions, i.e. use of transition metal-based complex (III), with conditions described in Example 2). An S/C in the range of 5000 to 20000 works with more or less 100% conversion rates, a decrease by around 30% is seen with an S/C in the range of 50000.

EXAMPLE 6: HYDROGENATION USING DIFFERENT RANGE OF TEMPERATURE AND AMOUNT OF BASE

To test the influence of the temperature and amount of base used in the hydrogenation step, production of the starting material is obtained as described in Example 2 (standard conditions) with removal of water, dissolving in methanol and use of transition metal-based complex (III). In addition to the standard conditions with the use of 5 mol % KOMe, 70° C. (see above), a different set-up contains 1 mol % KOMe, 90° C. No difference in yield is detected, thus still very good yield as described in Example 1 or 2.

The invention claimed is:

1. A process for producing D-sorbitol from sucrose, wherein the process comprises the steps of:
   (a) converting the sucrose to oxidized products substrate using glucose-fructose oxidoreductase (GFOR) enzyme; and thereafter
   (b) hydrogenating the oxidized products substrate in a hydrogenation step at a pressure of about 10 bar to about 60 bar and a temperature from about 30° C. to about 100° C. in the presence of a $H_2$ gas and a transition metal-based complex selected from the group consisting of transition metal based complexes according to formulas (III) to (VIII):

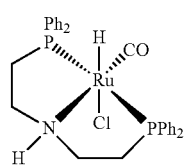
(III)

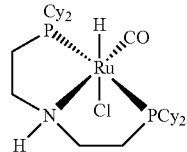
(IV)

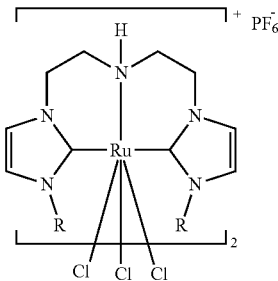
(V)

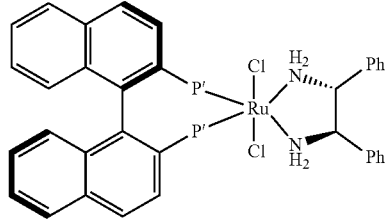
(VI)

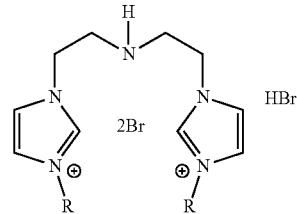
(VII)

Ir-bisNHC, R = Mes 0.5 equiv [Ir(COE)$_2$Cl]$_2$

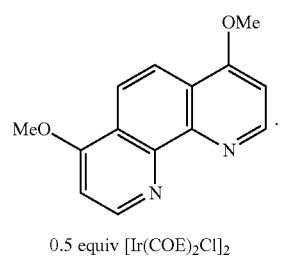
(VIII)

0.5 equiv [Ir(COE)$_2$Cl]$_2$

2. The process according to claim 1, wherein the process is carried out in the presence of a solvent selected from the group consisting of non-aqueous solvents, organic solvents and polar solvents.

3. The process according to claim 1, wherein a molar ratio of the substrate to the transition metal based complex is in the range of about 50 to about 100000.

4. The process according to claim 1, wherein the process is carried out in the presence of at least one base.

5. The process according to claim 4, wherein the at least one base comprises at least one alkoxide base.

6. The process according to claim 2, wherein the solvent is selected from the group consisting of alcohols, ethers and amides.

7. The process according to claim 2, wherein the solvent is selected from the group consisting of methanol, ethanol, propanol and tetrahydrofuran (THF).

8. The process according to claim 3, wherein the molar ratio of the substrate to the transition metal based complex is about 5000 to about 30000.

* * * * *